United States Patent [19]

Stamler et al.

[11] Patent Number: 5,346,599
[45] Date of Patent: Sep. 13, 1994

[54] CAPILLARY ZONE ELECTROPHORETIC DETECTION OF BIOLOGICAL THIOLS AND THEIR S-NITROSATED AND OXIDIZED DERIVATIVES

[76] Inventors: Jonathan Stamler, 220 Marlborough St., #1, Boston, Mass. 02116; Joseph Loscalzo, 50 Pacella Dr., Dedham, Mass. 02026

[21] Appl. No.: 9,469

[22] Filed: Jan. 26, 1993

[51] Int. Cl.$^5$ .................. G01N 27/26; G01N 27/447
[52] U.S. Cl. .............................. 204/180.1; 204/299 R
[58] Field of Search ...................... 204/180.1, 299 R

[56] References Cited

U.S. PATENT DOCUMENTS

| | | | |
|---|---|---|---|
| 5,002,964 | 3/1991 | Loscalzo | 514/423 |
| 5,025,001 | 6/1991 | Loscalzo et al. | 514/91 |

OTHER PUBLICATIONS

T. J. O'Shea and S. M. Lunte "Selective Detection of Free Thiols by Capillary Electrophoresis–Electrochemistry Using a Gold/Mercury Amalgam Microelectrode" Analytical Chemistry, vol. 65, No. 3 (1993) 247–250.

B. Lin Ling, W. R. G. Baeyens, & C. Dewaele "Capillary zone electrophoresis with ultraviolet and fluorescence detection for the analysis of thiols Applications to mixtures and blood" Analytica Chimica Acta vol. 255 No. 2 (1991) 283–288.

Chong, Saeho et al., "Bichemical and Pharmacological Interactions Between Nitroglycerin and Thiols", *Biochem. Pharm.* 42(7):1433–1439 (1991).

Grossman, Paul D. et al., "Effect of Buffer pH and Peptide Composition on the Selectivity of Peptide Separations by Capillary Zone Electrophoresis", *Anal. Biochem.* 173:265–270 (1988).

Holloway, C. J. et al., "The Simultaneous Analysis of Glutathione in Reduced and Oxidised Froms by Capillary Isotachophoresis", in *Analytical and Preparative Isotachophoresis*, Walter de Gruyter & Co., Berlin/New York, pp. 193–196 (1984).

Jocelyn, Peter C., "Spectrophotometric Assay of Thiols", *Methods in Enzymology* 143:44–67 (1987).

Kuhr, Werner G. et al., "Indirect Fluoescence Detection of Native Amino Acids in Capillary Zone Electrophoresis", *Anal. Chem.* 60:1832–1834 (1988).

Kowaluk, Elizabeth A. et al., "Spontaneous Liberation of Nitric Oxide Cannot Account for in Vitro Vascular Relaxation by S-Nitrosothiols", *J. of Pharm. Exp. Ther.* 255(3):1256–1264 (1990).

Park, Jeen-Woo et al., "An Unusually Stable S-Nitrosothiol from Glutathione", *Arch. Pharm. Res.* 2(4):257–258 (1989).

(List continued on next page.)

Primary Examiner—John Niebling
Assistant Examiner—John S. Starsiak, Jr.
Attorney, Agent, or Firm—Carella, Byrne, Bain, Gilfillan, Cecchi, Stewart & Olstein

[57] ABSTRACT

Individual thiols present in a biological sample are separated and identified using capillary electrophoresis. S-nitrosated and oxidized derivatives of thiols are also detected using capillary electrophoresis. In addition, capillary electrophoresis may be performed on samples which have been treated with an acid, so as to achieve a pH between 2.0 and 6.8, in order to further enhance detection. Separation and detection of S-nitrosated derivatives of thiols provides a means for monitoring the extent of a disease state associated with abnormal levels of nitric oxide. Such disease states include septic shock, cardiogenic shock, hypovolemic shock, atherosclerosis, hyperhomocysteinemia, venous thrombosis, arterial thrombosis, coronary occlusion, pulmonary embolism, cerebrovascular accidents, vascular fibrosis, ectopia lentis, osteoporosis, mental retardation, skeletal deformities, pulmonary hypertension, malignancy, infections and central nervous system disorders.

12 Claims, 6 Drawing Sheets

OTHER PUBLICATIONS

Stamler, Jonathan S. et al., "Endothelium–Derived Relaxing Factor Reacts with Protein Sulfhydryl Groups to Form Stable, Biologically Active S–Nitrosothiols", *Circulation* 84(4)[*Suppl. 2*]:II–672, Entry 2671 (Oct. 1991).

Stamler, Jonathan S. et al., "S–Nitrosylation of Proteins with Nitric Oxide: Synthesis and Characterization of Biologically Active Compounds", *PNAS USA* 89:444–448 (Jan. 1992).

Stamler, Jonathan S. et al., "Capillary Zone Electrophoretic Detection of Biological Thiols and Their S–Nitrosated Derivatives", *Anal. Chem.* 64:779–785 (1992).

Tsikas, D. et al., "Application of Capillary Isotachophoresis to the Analysis of Glutathione Conjugates", *J. of Chromatography* 470:191–199 (1989).

Yu, Margaret et al., "Attomole Amino Acid Determination by Capillary Zone Electrophoresis with Thermooptical Absorbance Detection", *Anal. Chem.* 61:37–40 (1989).

E. Jellum, A. K. Thorsrud, & E. Time "Capillary electrophoresis for diagnosis and studies of human disease, particularly metabolic disorders" Journal of Chromatography 559 (1991) 455–465.

D. Tsikas & G. Brunner "Application of capillary isotachophoresis to the analysis of glutathione conjugates" Journal of Chromatography 470 (1989) 191–199.

N. Mizobuchi, T. Ageta, K. Sasaki, & H. Kodama "Isotachophoretic analyses of cyctine homocystine, and cystathionine in urines from patients with inborn errors of metabolism" Journal of Chromatography 382 (1986) 321–325.

C. J. Holloway "Bimane conjugates of thiols: Detection and migration properties in isotachophoretic systems" Journal of Chromatography. 390 (1987) 101–110.

Y. Tanaka & W. Thormann "Capillary electrophoretic determination of S–carboxymethyl–L–systeine and its major metabolites in human urine: Feasibility investigation using on–column detection of non–derivatized solutes in capillaries with minimal electroosmosis"Electrophoresis, 11(9), (1990) 760–764.

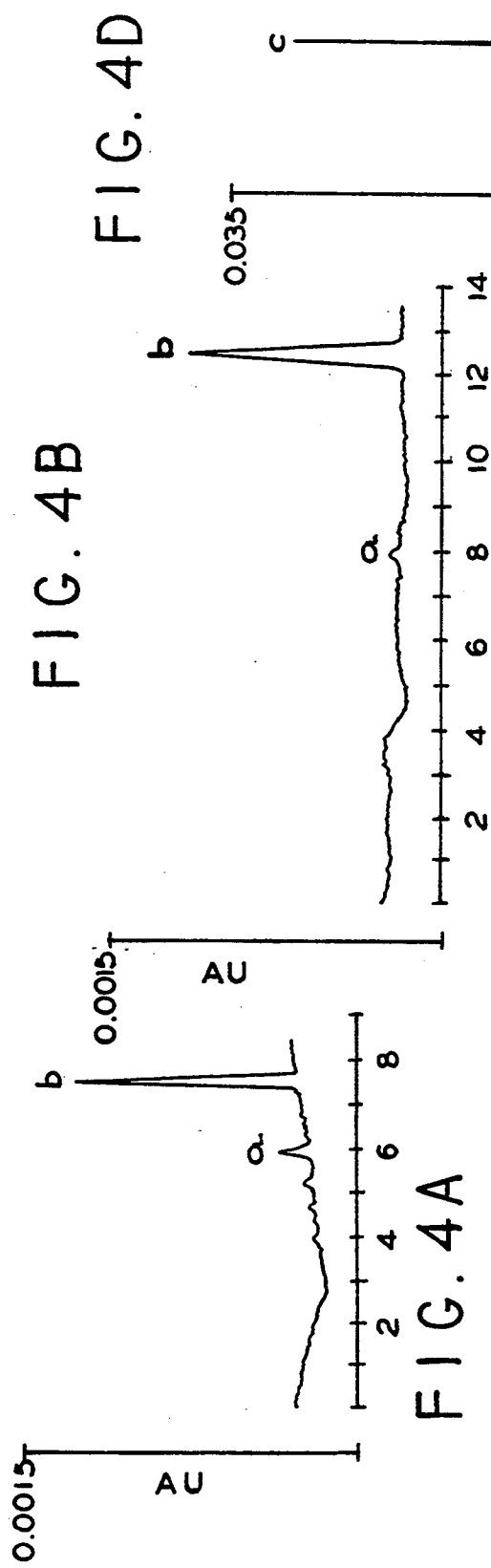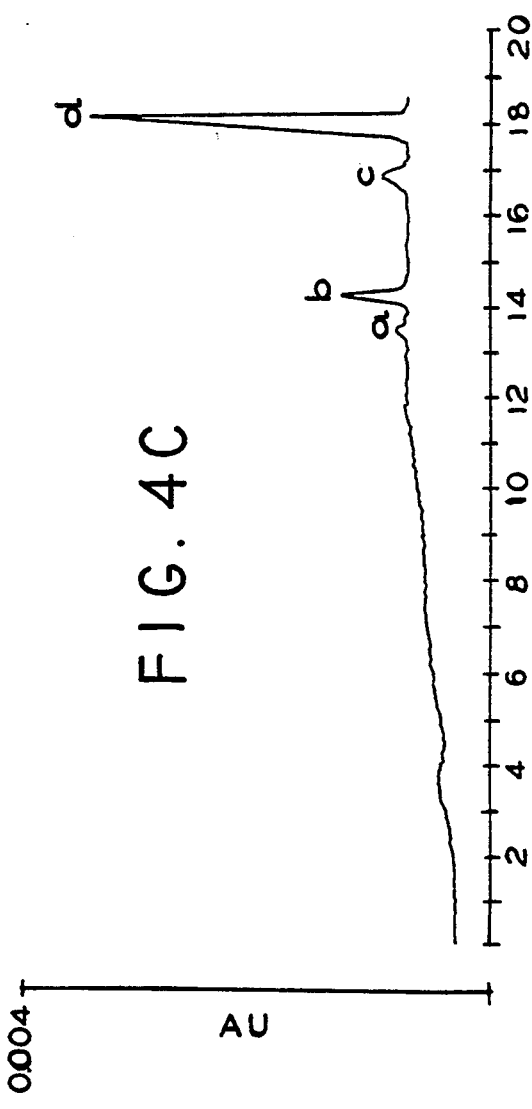

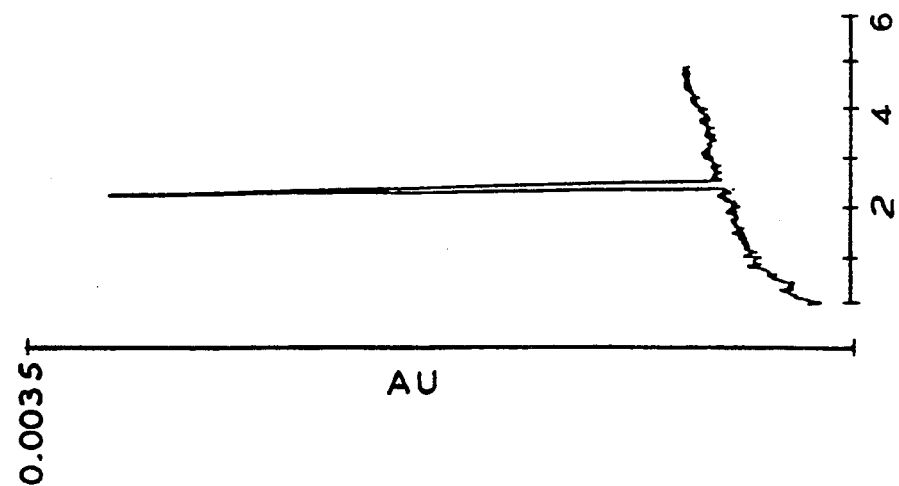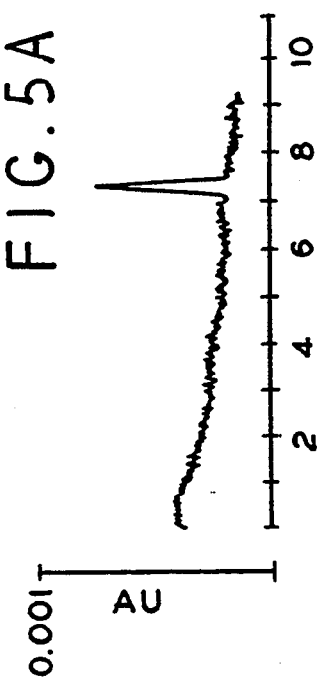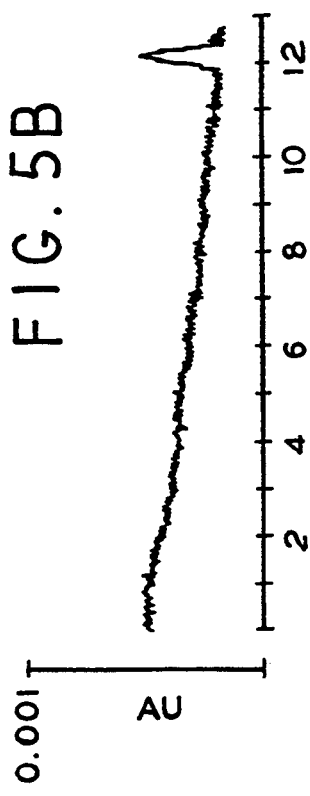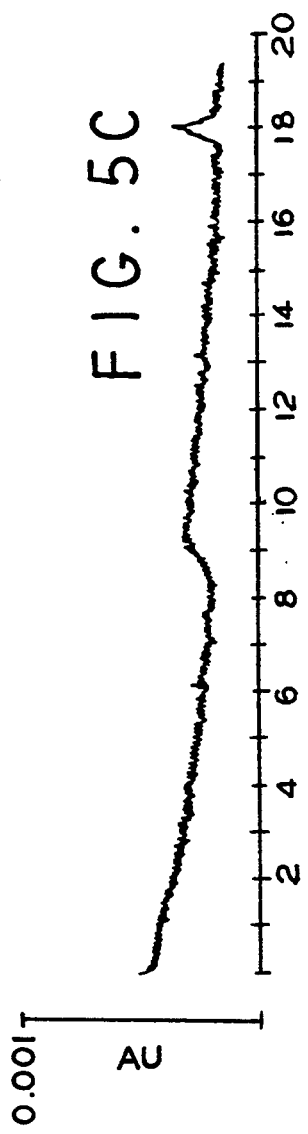

CAPILLARY ZONE ELECTROPHORETIC DETECTION OF BIOLOGICAL THIOLS AND THEIR S-NITROSATED AND OXIDIZED DERIVATIVES

BACKGROUND OF THE INVENTION

This invention was made with government support under HL40411, HL43344, National Research Fellowship F32 HL08177, and K04 HL02273 awarded by the National Institutes of Health. The government has certain rights in the invention.

Field Of The Invention

The invention relates to a method for separating and detecting individual thiols present in a sample, by subjecting the sample to capillary electrophoresis. This method is also used to detect S-nitrosated and oxidized derivatives of thiols. The invention provides an additional method in which the sample is treated with an acid in order to achieve a pH which is between 2.0 and 6.8, just prior to subjecting it to capillary electrophoresis.

Brief Description Of The Background Art

The fraction of sulfur existing as free sulfhydryl moieties (RSH) in eukaryotic cells largely resides in the low-molecular-weight compounds, glutathione, cysteine, and homocysteine (Jocelyn, *Biochemistry of the SH Group;* Academic Press: London/New York, pp. 1–46 (1972)). Although these compounds exploit unique aspects of sulfur chemistry to execute various thiol-specific biochemical functions, they share many physical properties and a common chemistry, as illustrated by the conversion of reduced thiols to S-nitrosothiols and thionitrites upon treatment with certain oxides of nitrogen. (Oae, S. et al., *Org. Prep. Proced. Int.* 15:165–198 (1983)). Each of the S-nitrosated biological thiol derivatives are reactive chemical species possessing innate antiplatelet and vasodilatory properties not manifested by equimolar amounts of thiol and nitric oxide alone (Loscalzo, J., *J. Clin. Invest.* 76:703–708 (1985); Ignarro et al., *J. Pharmacol. Exp. Ther.* 218:739–749 (1981); and Mellion et al., *J. Mol. Pharmacol.* 23:653–654 (1983)).

S-nitrosothiols are adducts that form readily under physiologic conditions from the reaction of nitric oxide with reduced low molecular weight thiols, and have potent vasodilatory and antiplatelet properties. These adducts have also been proposed as active intermediates in the biochemistry and metabolism of organic nitrates (Loscalzo, J., *J. Clin. Invest.* 76:703–708 (1985); Ignarro et al., *J. Pharmacol. Exp. Ther.* 218:739–749 (1981); Mellion et al., *J. Mol. Pharmacol.* 23:653–654 (1983)).

The relatively recent observation that the endothelium-derived relaxing factor (EDRF) possesses the biochemical and chemiluminescent properties of NO, has led to the suggestion that S-nitrosothiols exist as important biological intermediates in vascular smooth muscle and platelets as well (Palmer et al., *Nature* (London) 327:1020–1022 (1987)). In fact, it has been suggested that the chemical and spectrophotometric properties of EDRF more closely resemble those of S-nitroso-cysteine than NO (Myers et al., *Nature* 345:161–163 (1990)). S-nitrosothiols have half-lives than that of NO, and like EDRF, possess vasorelaxant activity that is mediated through activation of guanylate cyclase (Kowaluk et al., *J. Pharmacol. Exp. Ther.* 256:1256–1264 (1990)). Importantly, these adducts serve to stabilize NO in vivo, in a form that preserves its biological activity.

The most widely used method for the detection of S-nitrosothiols involves the assay of free nitrite, in diazotization reactions with sulfanilic acid in the presence and absence of $HgCl_2$, with the latter reagent facilitating the hydrolysis of the S-NO bond (Snell et al., *Calorimetric Methods of Analysis,* 3rd ed. D. Van Nostrand Co., New York pp. 804 (1949); Saville, *Analyst* 83:670–672 (1958)). While this method is useful in quantitative analyses, it is limited in that it is relatively insensitive, and cannot elucidate the chemical identity of the parent S-nitrosothiol compound.

Reverse-phase high-performance liquid chromatography (RP-HPLC) has been utilized for preparations of organic S-nitrosothiols and has proven helpful in limited analyses of the biological S-nitrosothiols (Oae et al., *J. Chem. Soc.* 38:913–917 (1978); Myers et al., *Nature* 345:161–163 (1990), Fung et al., *J. Pharmacol. Exp. Ther.* 246:524–530 (1988)). However, the sample preparation required for this method is a formidable obstacle, because of the inherent instability of the S-NO bond. Furthermore, such preparative modification results in sample dilution and secondarily affects the analyte, thus altering its chemical and biological activity.

High perthfinance capillary electrophoresis (HPE) is a relatively new high-resolution electrophoretic technique that separates compounds on the basis of their molecular weight and net charge. The efficiency of this method has already been demonstrated for several small molecules, including amino acids and peptides (Kahr et al., *Anal. Chem.* 60:1832–1834 (1988); Yu et al., *Anal. Chem.* 61:37–40 (1989); and Grossman et al., *Anal. Biochem.* 173:265–270 (1988)). Very recently, investigators have reported the use of HPE for the separation of conjugated forms of one thiol, glutathione, as well as the resolution of reduced glutathione from its disulfide; these observations have been confirmed in alkaline medium (Tsikas et al., *J. Chromatogr.* 470:191–199 (1989); Holloway et al., *Analytical and Preparative Isotachophoresis,* Walter de Gruyer: Berlin/New York, pp. 193–196 (1984)). However, while HPE has been used to detect a single thiol, glutathione, this method has not been used to separate and distinguish individual thiols which are present in a sample. Moreover this method of glutathione detection is limited by oxidation of the thiol to disulfide.

Given the biological importance of thiols and their S-nitrosated and oxidized derivatives, a need exists for a simple method for separating and identifying these compounds.

SUMMARY OF THE INVENTION

The invention relates to a method for separating and detecting individual thiol compounds in a biological sample comprising subjecting said sample to capillary electrophoresis.

The invention also relates to a method for separating and detecting individual thiol compounds in a biological sample comprising the steps: (a) determining the elution time of known individual thiols to establish thiol standards; (b) subjecting said biological sample to capillary electrophoresis; and (c) comparing the elution times obtained for each component present in the sample, to the known elution times of the thiol standards prepared in step (a) to determine the identity of each individual thiol compounds present in the sample.

The invention also relates to a method for separating and detecting individual S-nitrosothiol compounds in a biological sample comprising subjecting said sample to capillary electrophoresis.

The invention also relates to a method for separating and detecting individual S-nitrosothiol compounds in a biological sample comprising the steps: (a) determining the elution time of known individual nitrosothiols to establish S-nitrosothiol standards; (b) subjecting said biological sample to capillary electrophoresis; and comparing the elution times obtained for each component present in the sample to the known elution times of the S-nitrosothiol standards prepared in step (a) to determine the identity of each individual thiol compound present in the sample.

The invention further relates to a method for separating and detecting oxidized derivatives of thiol compounds in a biological sample comprising subjecting said sample to capillary electrophoresis.

The invention also relates to a method for separating and detecting oxidized derivatives of individual thiol compounds in a biological sample comprising the steps: (a) determining the elution time of known oxidized derivatives of individual thiol compounds to establish oxidized derivative standards: (b) subjecting said biological sample to capillary electrophoresis; and (c) comparing the elution times obtained for each compound present in the sample to the known elution times of the oxidized derivative standards prepared in step (a) to determine the identity of each individual oxidized thiol derivative present in the sample.

The invention further relates to the methods of the invention wherein the sample is treated with an acid prior to subjecting it to capillary electrophoresis. In particular, treatment of the sample with acid results in a sample pH between 2.0–6.8.

The invention further relates to the methods of the invention wherein the biological sample is selected from the group consisting of blood, serum, urine, cerebrospinal fluid, semen, synovial fluid, peritoneal fluid, sputum, intestinal secretions, corneai fluid, amniotic fluid, stool, saliva and sweat.

The invention further relates to the methods of the invention wherein capillary electrophoresis is conducted at a temperature range of 4° C.–37° C.

The invention further relates to a method for monitoring the extent of a disease state associated with abnormal levels of nitric oxide, nitrosonium (NO+) or nitroxyl (NO−) comprising the method for determining S-nitrosothiol levels in the biological fluids of a patient. In particular, said disease state may be selected from the group comprised of septic shock, cardiogenic shock, hypovolemic shock, atherosclerosis, hyperhomocysteinemia, venous thrombosis, arterial thrombosis, coronary occlusion, pulmonary embolism, cerebrovascular accidents, vascular fibrosis, ectopia lentis, osteoporosis, mental retardation, skeletal deformities, pulmonary hypertension, malignancy, infections and central nervous system disorders, pulmonary diseases, gastrointestinal disorders and renal disorders.

Figure 1:
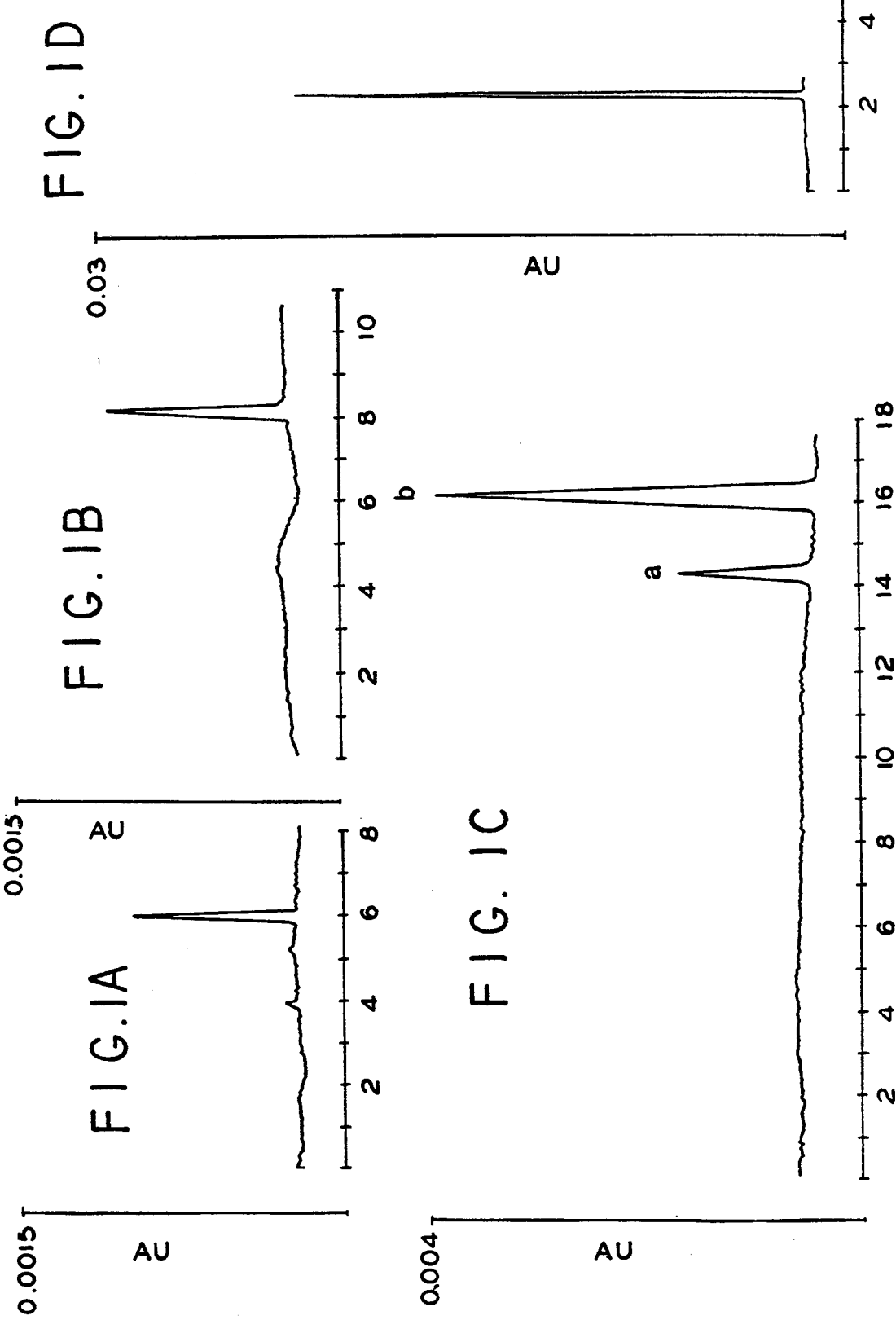
FIG. 1

Electropherograms of biological thiols;
A. homocysteine (250 μM);
B. cysteine (500 μM);
C. glutathione (500 μM).
D. N-acetylcysteine (500 μM).

Conditions (A-C); sample buffer, 0.01M sodium phosphate, 0.01N HCI, pH 2.3; positive polarity at 11 kV; absorbance, 200 nm.

Conditions (D): sample buffer, 0.01 sodium phosphate, 0.01 nHCI, pH 5.0; negative polarity at 11 kV; absorbance, 200 nm.

FIG. 2

Electropherograms of disulfides:
A. homocysteine (250 μM);
B. cystine (250 μM);
C. glutathione disulfide (250 μM).

Conditions: sample buffer, 0.01M sodium phosphate 0.01N HCI, pH 2.3; positive polarity at 11 kV; absorbance, 200 nm.

FIG. 3

Electropherogram of a sample mixture of equimolar (167 μM) homocystine, cystine, and glutathione disulfide, under acidic conditions.

Conditions: sample buffer, 0.01M sodium phosphate, 0.01N HCl, pH 2.3; positive polarity at 11 kV; absorbance, 200 nm.

FIG. 4

Electropherograms of S-nitrosothiols:
A. S-nitroso-homocysteine, with 92% conversion of 250 μM homocysteine (peak a) to S-nitroso-homocysteine (299 μM) (peak b);
B. S-nitroso-cysteine, with 91% conversion of 250 μM cysteine (peak a) to S-nitroso-cysteine (228 μM) (peak b);
C. S-nitroso-glutathione, with 92% conversion of 250 μM glutathione (peak c) to S-nitroso-glutathione (170 μM) (peak d) and to two additional unidentified peaks (peaks a and b);
D. S-nitroso-N-acetylcysteine, with 82% conversion of 500 μM N-acetylcysteine (peak b) to S-nitroso-N-acetylcysteine (410 μM) (peak d) (peak a is unidentified; however, it most likely represents N-acetylcysteine disulfide).

Conditions (A-C); sample buffer, 0.01M sodium phosphate, 0.01N HCI pH 2.3; positive polarity at 11 kV: absorbance, 200 nm.

Conditions (D): sample buffer, 0.01M sodium phosphate, 0.01N HCI pH 5.0; negative polarity at 11 kV; absorbance, 200 nm.

FIG. 5

Electropherograms of S-nitrosothiols:
A. S-nitroso-homocysteine
B. S-nitroso-cysteine
C. S-nitroso-glutathione
D. S-nitroso-N-acetylcysteine Conditions: Same as FIG. 4, except that absorbance was measured at 320 rim.

FIG. 6

Separations of thiols and their S-nitrosated derivatives, with concentrations determined from the dam of Table III.

A. Homocysteine (a); S-nitroso-homocysteine (b); cysteine (c); and S-nitroso-cysteine (d).
B. Homocysteine (b); cysteine (d); and glutathione (e).

C. S-nitroso-homocysteine (a) and S-nitroso-glutathione (b).

Conditions (A-C): sample buffer, 0.01 sodium phosphate, 0.01 N HCl, pH 2.3; positive polarity at 11 kV; absorbance (A, B) 200 nm.

DESCRIPTION OF THE PREFERRED EMBODIMENTS

Thiols and their nitrosated and oxidized derivatives are important compounds in biological systems. In particular, the S-nitrosated derivatives of thiols (S-nitrosothiols) serve as important biological intermediates in smooth muscle and platelet function, and represent a biological reservoir of bioactive nitric oxide. Therefore, in order to provide a means for identifying these important compounds, the inventors have discovered a method which enables the separation and detection of individual thiols and their S-nitrosated and oxidized derivatives.

In one embodiment, the invention relates to a method for separating and detecting individual thiols in a biological sample comprising subjecting the sample to capillary electrophoresis. It is appreciated that the analytical parameters and conditions for conducting capillary electrophoresis are determined without undue experimentation using routine methods which are widely available to those of skill in the art.

A particular embodiment of the claimed invention relates to a method for separating and detecting individual style compounds in a biological sample by (a) determining the elution time of known individual thiols to establish thiol standards; (b) subjecting the biological samples to capillary electrophoresis; and (c) comparing the elution times obtained for each component present in the sample to the known elution times of the thiol standards prepared in step (a) to determine the identity of individual thiol compounds present in the sample.

Examples of thiols which are detected include, but are not limited to, cysteine, homocysteine, N-acetylcysteine, glutathione, penicillamine and captopril. Biological samples include, but are not limited to blood, serum, urine, cerebrospinal fluid, semen, synovial fluid, peritoneal fluid, intestinal secretions, sputum, stool, saliva, corneal fluid, amniotic fluid and sweat.

An additional embodiment of the claimed invention relates to a method for separating and detecting individual nitrosothiols present in a biological sample, comprising subjecting the sample to capillary electrophoresis. Examples of S-nitrosothiols which are detected include, but are not limited to, S-nitroso-cysteine, S-nitroso-homocysteine, S-nitroso-N-acetylcysteine, S-nitroso-glutathione, S-nitroso-captopril, S-nitroso-penicillamine and S-nitro-proteins.

A particular embodiment of this claimed method relates to a method for separating and detecting individual S-nitrosothiol compounds in a biological sample by (a) determining the elution time of known individual S-nitrosothiols to establish S-nitrosothiol standards: (b) subjecting said biological sample to capillary electrophoresis; and (c) comparing the elution times obtained for each component present in the sample to the known elution times of the S-nitrosothiol standards prepared in step (a) to determine the identity of each individual thiol compound present in the sample.

Another embodiment of the claimed invention relates to a method for separating and detecting oxidized derivatives of thiols in a biological sample, by subjecting the sample to capillary electrophoresis. Examples of oxidized derivatives which are detected include, but are not limited to homocystine, cystine, glutathione disulfide, homocysteine thiolactone, and related sulfenic, sulfinic and sulfonic acids.

A particular embodiment of the claimed invention relates to a method for separating and detecting oxidized derivatives of individual thiol compounds in a biological sample by (a) determining the elution time of known oxidized derivatives of individual thiol compounds to establish oxidized derivative standards; (b) subjecting said biological sample to capillary electrophoresis; and (c) comparing the elution times obtained for each compound present in the sample to the known elution times of the oxidized derivative standards prepared in step (a) to determine the identity of each individual oxidized thiol derivative present in the sample.

A particular embodiment of the invention relates to a method in which the biological sample which is subjected to capillary electrophoresis, is treated with an acid in order to lower the pH of the sample. In this manner, the sample is diluted in an acidic reagent, such as HCl, to obtain a pH which is preferably in the range of 2.0 to 6.0. It is appreciated that one of skill in the art will be able to determine the appropriate pH for a given sample, using routine methods and without requiring undue experimentation. For example, pH 6.0 (negative polarity) is especially preferable for glutathione detection; under these conditions, elution is rapid and its oxidation is entirely limited. N-acetylcysteine is preferably detected at PH 5.0 (+polarity). Certain other thiols may be detected at a pH of 2-3.

Another particular embodiment of the invention relates to a method in which capillary electrophoresis is conducted at a temperature which is lower than 37° C. In particular, a temperature of 4° C. is preferable. The inventors have discovered that subjecting samples to capillary electrophoresis at lower temperatures further enhances the analytic specificity of capillary electrophoresis, under acidic conditions, by limiting the formation of S-nitrosothiol and the further oxidation of the SH group.

In a further embodiment of the claimed invention, the methods described above may be utilized to determine the presence of a disease state which involves abnormal levels of thiols, S-nitrosothiols or oxidized derivatives of thiols, by monitoring the levels of these compounds in the biological fluids of a patient.

As described by the inventors, S-nitrosothiols represent a pool of bioactive nitric oxide in physiological systems. Therefore, in disease states in which the pathogenesis derives from the effects of abnormal levels of nitric oxide, nitrosonium or nitroxyl (collectively referred to as NO), these analytical methods provide a means for the clinician to determine the presence of, and monitor the extent of the disease state. Such information enables the clinician to determine the appropriate pharmacological intervention necessary to treat such a disease state. Examples of such disease states include, but are not limited to, septic shock, cardiogenic shock, hypovolemic shock, atherosclerosis, hyperhomocysteinemia, venous thrombosis, arterial thrombosis, coronary occlusion, pulmonary embolism, cerebrovascular accidents, vascular fibrosis, ectopia lentis, osteoporosis, mental retardation, skeletal deformities, pulmonary hypertension, other respiratory disorders such as asthma, malignancy, infections and renal and central nervous system disorders. Furthermore, the use of these methods is not limited to these diseases. It is predicted that the detection of S-nitrosothiols will be of use in detecting biologically active nitric oxide equivalents in any organ system in which nitric oxide is implicated.

In addition, the detection of biological thiols and their oxidized derivatives have significant clinical applications as well. For example, monitoring glutathione levels is useful in clinical management of hepatic disorders. In addition, thiols such as cysteine, have been shown to be cytotoxic and also to contribute to atherogenesis through the generation of reactive oxygen species. Finally, monitoring the levels of various thiols is beneficial in evaluation and treatment of connective tissue disorders.

The invention provides an analytical method that enables the detection of thiols, as well as their S-nitrosated and oxidized derivatives in a biological sample. The method provides important information which is of significant value in a variety of research and clinical situations.

Having now generally described the invention, the same will be more readily understood through reference to the following example which is provided by way of illustration, and not intended to be limiting the present invention.

The entire text of all publications cited above and below and hereby incorporated by reference.

EXAMPLES

EXAMPLE 1

Detection Of Thiols, And Their Oxidized And Nitrosated Derivatives

METHODS AND MATERIALS

Chemicals And Solutions

Glutathione, L-cysteine, D, L-homocysteine, homocysteine thiolactone (free base and hydrochloride), cystine, homocystine, bradykinin triacetate, iodacetamide, and 2-mercaptoethanol were purchased from Sigma Chemical Co. (St. Louis, Mo.). Glutathione disulfide and N-acetylcysteine were purchased from Aldrich Chemical Co., (Milwaukee, Wis.). Sodium nitrite was purchased from Fisher Scientific (Fairlawn, N.J.).

Apparatus

The isotachophoretic analyses were per/brined on the Bio-Rad HPE-100 capillary electrophoresis system (Bio-Rad, Richmond, Calif.) fitted with a silica-coated capillary (20 cmx 25 $\mu$M). Electrophoretic separations were detected on-line and recorded with a Model 1321 single-pen strip chart recorder (Bio-Rad, Richmond, Calif.) programmed at a chart speed of 1.0 cm/min with a rise time of 1 s. Samples were injected using Hamilton syringes, and analyses were performed at room temperature.

1. Sample Preparation a. S-Nitrosothiols.

S-nitrosothiols were prepared at 25° C. by reacting equimolar (100 mM)concentrations of reduced thiol with $NaNO_2$ in 1N HCI (Loscalzo, J., *J. Clin. Invest.* 76:703–708 (1985)). Solutions turned from clear, to various shades of red instantaneously, indicating completion of the reaction.. The S-nitrosothiols could be identified by visible absorption spectroscopy having characteristic absorption maxima at 320 and 550 nm. (Loscalzo, J., *J. Clin. Invest.* 76:703–708 (1985), lgnarro et al., *J. Pharmacol. Exp. Ther.* 218:739–749 (1981) and Ignarro et al., *FEBS Lat.* 11:275–278 (1980)). Because of the instability of S-nitroso derivatives, fresh samples were made at hourly intervals and stored in 1N HCl at 4° C. until use.

Immediately prior to electrophoresis, S-nitrosothiols were diluted in all cases in 0.0.1N HCI, 0.01M sodium phosphate. The pH of the sample solution for S-nitroso-glutathione, S-nitroso-cysteine, and S-nitrosohomocysteine, was 2.3, and for S-nitroso-N-acetylcysteine it was 5.0. Concentrations of stock solutions were determined by standard methods (Saville, *Analyst* 83:670–672 (1958)).

b. Thiols, Thiolactone and Disulfides

Stock solutions of thiols were first prepared by dissolving these compounds in 1N HCI to achieve a final concentration of 100 mM. Owing to their propensity to autooxidize, even at acidic pH, fresh preparations of thiols were made at hourly intervals, protected from light, and stored on ice at 4° C. until immediately prior to electrophoresis (Hopkins, *J. Biol. Chem.* 84:269–320 (1929) and Jocelyn, *Biochemistry of the SH Group;* Academic Press: London/New York pp. 95 (1972)). Samples were then diluted in 0.01 N HCl, 0.01 sodium phosphate to obtain a pH of 2.3. Concentrations of the stock solutions were determined by reaction with 5,5 '-dithi-obis(2-nitrobenzoic acid) (DTNB) (Ellman, *Arch. Biochem. Biophys.* 82:70–77 (1959)).

Fresh stock solutions of homocysteine thiolactone were prepared daily in warm 1N HCI, and dilutions in phosphate buffer were made immediately prior to use, as described above for thiols. The expected stability of homocysteine thiolactone in 1N HCI was confirmed by demonstrating the inaccessibility of the ring sulfur to thiol-disulfide exchange in the reaction with DTNB over a 6-hour period (Riegel et al., *J. Biol. Chem.* 112:149–154 (1935)). Stability was later also confirmed by HPE for up to 48 h (Ellman, *Arch. Biochem. Biophys.* 82:70–77 (1959)).

Similar preparatory steps were taken in the case of disulfide sample preparation, with the single exception that stock solutions in 1N HCl were immediately diluted in 0.01N HCl, 0.01N sodium phosphate (pH 2.3), to avoid the potential electrophilic cleavage of disulfides in more strongly acidic media (Jocelyn, *Biochemistry of the SH Group;* Academic Press: London/New York pp. 117–136 (1972)). Fresh solutions of disulfides were prepared every 3–4 hours and stored on ice at 4° C. until use. Concentrations of stock solutions were determined by failure to react in the Saville reaction (without mercurous ion) and by direct detection of disulfides after sulfitolysis with 2-nitro-5-thiosulfobenzoate (NTSB) (Thannhauser et al., *Anal. Biochem.* 138:181–186 (1984)).

In selected experiments thiols and their sulfides were dissolved in 0.1M borate, followed by dilutions as necessary for a sample solution in 0.01M borate, pH 8.0. To minimize spontaneous oxidation of thiols, and nucleophilic cleavage of disulfides, fresh samples were prepared immediately prior to use (Hopkins, *J. Biol. Chem.* 84:269–320 ( 1929); Jocelyn, *Biochemistry of the SH Group;* Academic Press: London/New York pp. 95 (1972); and Jocelyn, *Biochemistry of the SH Group;* Academic Press: London/New York pp. 117–136 (1972)).

c. Thiol Derivatization

Carboxyamidation of reduced thiols was performed with a 2.5-fold molar excess of iodoacetamide at neutral pH for 60 rain at 37° C. (Smythe, *J. Biol. Chem.* 114:601–608 (1936)). Reaction mixtures were protected from light with the use of aluminum toil. Samples were then diluted into a final sample solution containing 0.01N HCl, 0.01M sodium phosphate (pH 2.3).

2. Electrophoresis

To initiate analyses, the capillary and electrode reservoirs were filled with electrophoresis buffer. This inlet was then flushed with deionized water, and a 10-$\mu$L sample solution was loaded for 9 s at 11 kV. The inlet electrode reservoir was subsequently flushed with electrophoresis buffer and the sample run performed at 11 kV. Equally reproducible electrophoresis was also accomplished using a constant current of 20 $\mu$A. For free zone electrophoresis in phosphate buffer at pH 2.5, the polarity of the internal power supply was set for the migration of cations toward the detector (+polarity). Conversely, analyses performed in phosphate buffer at pH 5.0 or 6.0, or borate at pH 8.0, utilized negative polarity for the migration of anions. Between analyses the capillary was flushed with separation buffer.

Eluted volumes were monitored at 200 nm, and confirmatory evidence of S-nitrosothiol detection was obtained at 320 nm (Jocelyn, P. C. *Methods in Enzymology*, Jacoby, Griffith, eds.; Academic Press: New York Vol. 143, pp. 63-66 (1987)). Optimal sensitivity was achieved at 200 nm. S-nitrosothiols possess secondary absorbance maxima in the range 320-360 nm and at approximately 550 mn (Jocelyn, *Biochemistry of the SH Group;* Academic Press: London/New York, pp. 1-46 (1972); Oae, S. et al., *Org. Prep. Proced. Int.* 15:165-198 (1983); Jocelyn, P. C. *Methods in Enzymology.* Jacoby, Griffith, eds.; Academic Press: New York Vol. 143, pp. 63-66 (1987); Loscalzo, J., *J. Clin. Invest.* 76:703-708 (1985); Ignarro et al., *FEBS Lett.* 11:275-278 (1980)). Absorbance at 320 nm was chosen for specific S-nitrosothiol detection because it was more sensitive and thus more useful than 550 nm, in these analyses.

RESULTS

The general expression for relating electrophoretic mobility ($\mu_e$) of peptides to their molecular size and charge can be given as:

$$\mu_e = v/E = q/(6\pi\eta\bar{R}_h);$$

wherein $\mu_e$ is the electrophoretic mobility, $v$ is the migration velocity, E is the electric field strength, q is the solute charge, r/is the solvent viscosity, and $\bar{R}_h$ is the mean Stoke's (hydrodynamic) radius of the peptide. In analyzing simple molecules that do not exhibit notable intramolecular interactions under a given set of solvent conditions, this equation provides a useful estimate of relative electrophoretic mobility that may be derived from a calculation of charge-to-mass ration (=effective charge).

The calculated net charges of homocysteine, cysteine, and glutathione at pH 2.3 are 0.44, 0.27 and 0.35, respectively (Pirie et al., *J. Biol. Chem.* 84:321-333 (1929); *Handbook of Biochemistry and Molecular Biology*, CRC Press, Boca Raton, Fla. (1982)). Effective charge calculations predict the electrophoretic mobility of homocysteine to be greater than cysteine, and that of cysteine to be greater than glutathione. On the basis of the observed elution of homocysteine at 5.92±0.15 rain, the predicted migration times ($t_p$) of the other thiols and their S-nitrosated derivatives have been calculated (Table 1) and show an excellent concordance with the observed migration times ($t_m$) (R=0.9919, P=0.0001).

a) Thiols And Their Oxidized Derivatives

FIG. 1 (A-D) provides representative electropherograms of homocysteine (A), cysteine (B), glutathione (C), and N-acetylcysteine (D). The latter thiol, a minor metabolite of cysteine, has received a great deal of attention in the context of nitrate metabolism and is included in our analysis for this reason. N-Acetyl-cysteine does not elute under the same conditions as the other biological thiols (FIG. 1D), prestonably as a result of the neutralizing influence of the negatively charged acetyl group on the effective charge of the molecule at pH 2.3. Commercially available glutathione provides another notable exception in that it elutes as two tully resolved peaks (FIG. 1C), the smaller of which (peak a) corresponds to contaminant glutathione disulfide, and the latter (b) to reduced glutathione. According to the concentration-response data of Table III, this particular preparation of reduced glutathione contained approximately 10% glutathione disulfide, a value that was confirmed with the DTNB reaction. Glutathione was further studied in phosphate buffer (pH 6.0) using negative polarity. Under these conditions, it elected at approximately 1.5 minutes as a single peak that was fully resolved from the disulfide.

Figure 2:
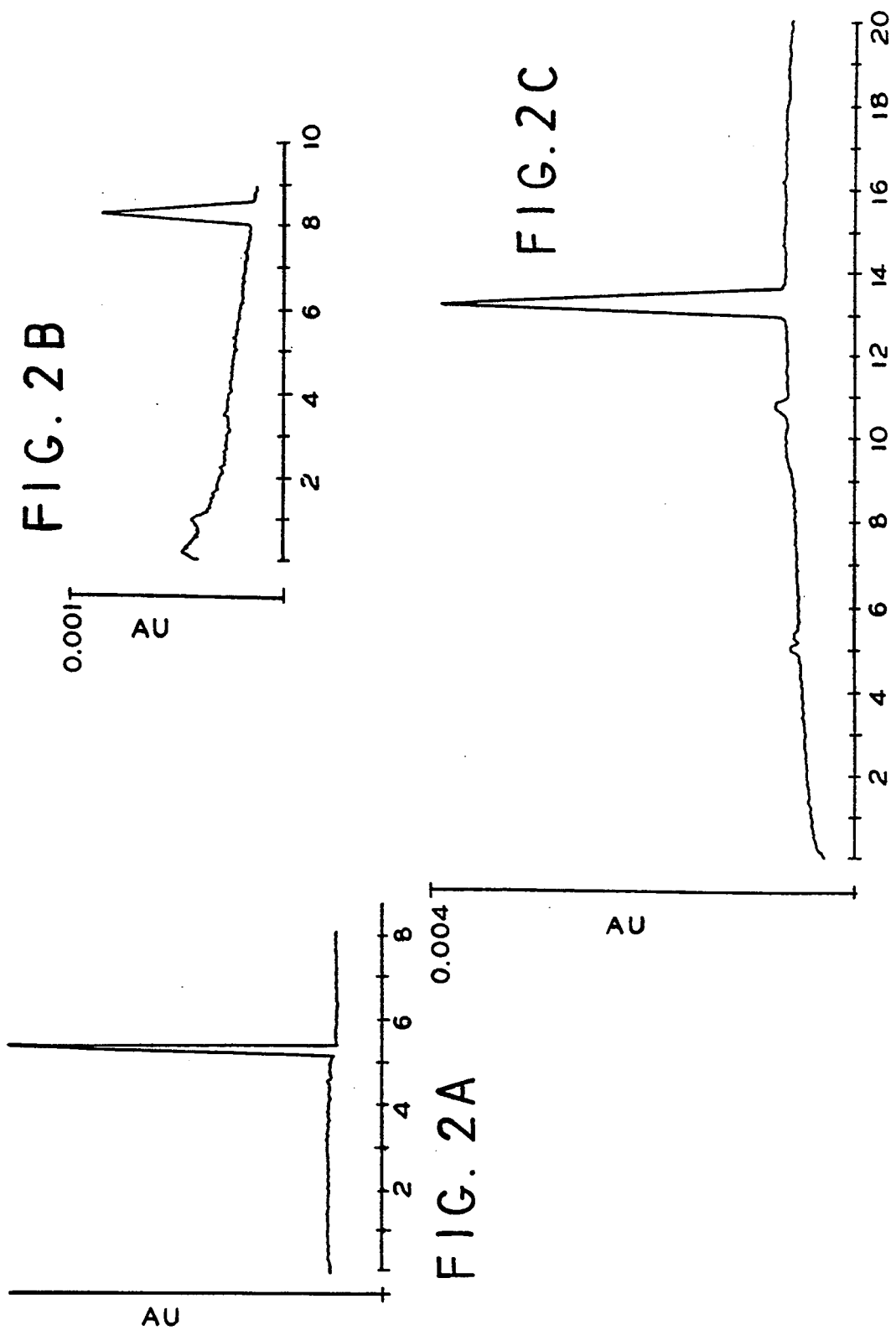
Figure 3:
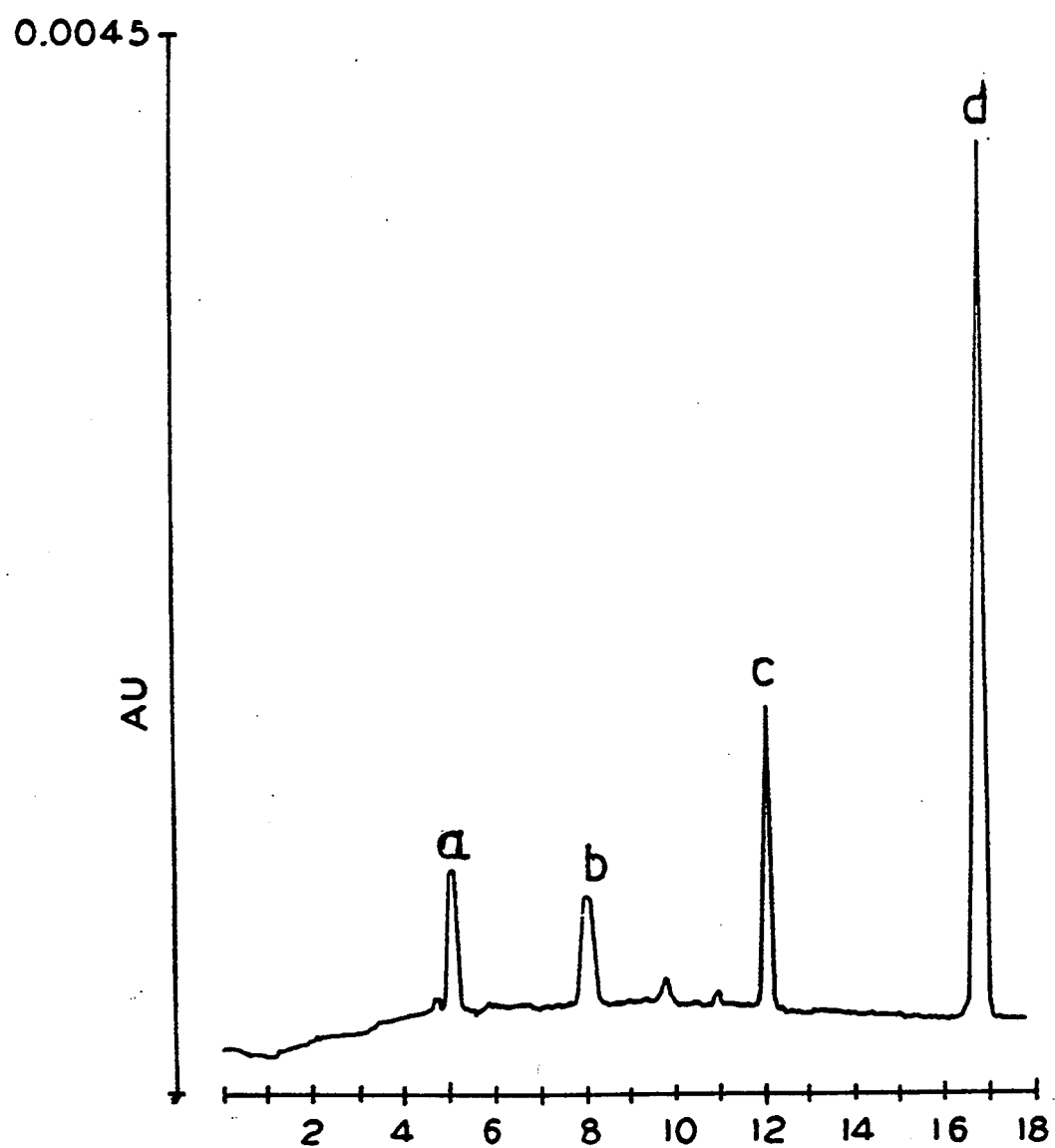

The migration of relevant homodisulfides is illustrated in FIG. 2. Distinct differences in migration are apparent, enabling for clear differentiation among disulfides in solutions containing several of these compounds (FIG. 3). The peak of homocysteine is also fully resolved from those of its disulfide and thiolactone derivatives, with the latter forming spontaneously from the reduced thiol under acidic conditions. (Rodgers et al., *J. Clin. Invest* 77:1909-1916 (1986); McCully et al., *Res. Commun. Chem. Pathol. Pharmacol.* 56:349-360 (1987)). In contrast, free zone capillary electrophoresis cannot accurately separate cysteine from cystine under these conditions. However, derivatization of cysteine by methods such as carboxyamidation ($t_m$=11.0 rain, n=2) and S-nitrosation, provides a simple means of achieving this separation.

The reproducibility of HPE in the above analysis is evidenced by the small standard deviations in migration times for the biological thiols and their oxidized derivatives, as shown in Table II. In addition, excellent linearity is demonstrated in plots of peak height vs concentration with correlations coefficients $\geq 0.99$ in each case (Table III).

An example of the applicability of this method to analysis of a variety of disulfides is shown in FIG. 3, in which electrophoresis was performed on a mixture of equimolar amounts of homocystine, cystine, and glutathione disulfide. As shown in FIG. 3, the electropherogram demonstrates tour fully resolved peaks corresponding in concentration (cf. Table IID to homocystine (102 $\mu$M) (peak a), cystine (145 $\mu$M) (peak b), and reduced glutathione (217 $\mu$M) (peak d), with an additional unidentified peak noted at 11.9 min (peak c). On the basis of the quantitative discrepancy between injected and detected solute as well as theoretical predictions, peak c is identified as glutathionehomocysteine mixed disulfide. Thus, the electropherogram implicates the electrophilic cleavage mechanism for mixed disulfide formation under acidic conditions.

Peak heights for homocystine and reduced glutathione account for 61% and 65% of the injected sample disulfides, respectively, suggesting that the unknown peak is glutathione-homocysteine disulfide. This contention is supported by the estimated migration time of 10.6 min for glutathione-homocysteine disulfide, based on a calculation of effective charge using the pKs of the individual thiols.

b) Detection of S-Nitrosothiols.

The electropherograms of S-nitroso-homocysteine, S-nitroso-cysteine, S-nitroso-glutathione, and S-nitroso-N-acetylcysteine are shown in FIG. 4(A–D).

Confirmatory evidence for the detection of these S-nitrosothiol adducts was provided by monitoring absorbance at 320 nm (FIG. 5). Reduced thiols and their disulfides were not detectable at this wavelength.

As predicted above (Table I), the S-nitrosated derivatives exhibited slower electrophoretic mobilities than their corresponding thiols (Table II). It is again noteworthy that the conditions for electrophoresis of S-nitroso-N-acetylcysteine were exceptional (pH 5.0, negative polarity). Linearity in the relationship between peak heights and concentration is also excellent with correlation coefficients $\geq 0.99$ (Table Ill).

In the case of S-nitroso-glutathione, four peaks were detected at 200 nm. The major peak of slowest electrophoretic mobility is identified as the S-nitrosothiol on the basis of predicted elution times (Table I), the coincident loss of the peak of reduced glutathione (FIG. 1), and the absorbance of this peak at 320 nm. The minor peak immediately preceding the S-nitrosothiol is identified as reduced glutathione on the basis of its migration time and is the result of incomplete nitrosation during synthesis or S-nitrosothiol decomposition during electrophoresis. The other two peaks remain unidentified. It is likely, however, that one of these is glutathione disulfide that forms as a result of spontaneous decomposition of the S-nitrosothiol as it traverses the capillary (Jocelyn, Biochemistry of the SH Group; Academic Press: London/New York, pp. 1–46 (1972)). The peak height of S-nitroso-glutathione accounts for $72 \pm 6\%$ (n=4) of the sum of the four peak thus preserving the linearity between the sum total peak height and sample concentration ($R \geq 0.99$).

Detection of S-nitroso-glutathione was also performed using negative polarity in phosphate buffer at pH 6.0. Under these conditions, rapid elution of a single peak was observed (t=2.0 rain), and the compound was fully resolved from glutathione. These are optimum conditions for glutathione and its S-nitrosated derivative but not for other thiols.

Figure 6A:
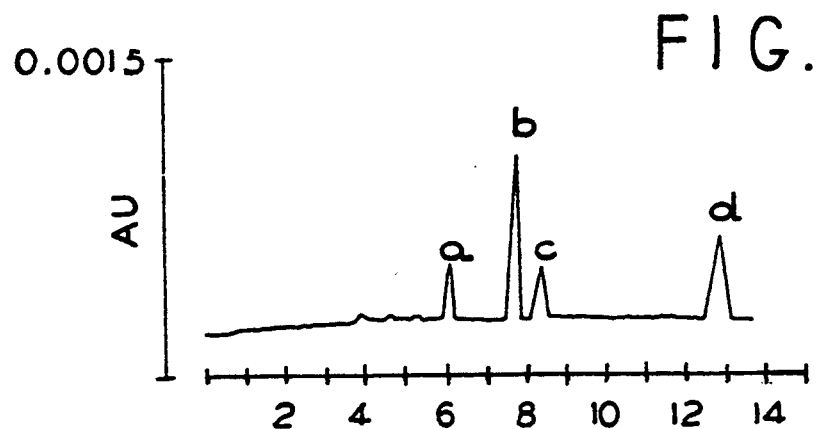
Figure 6B:
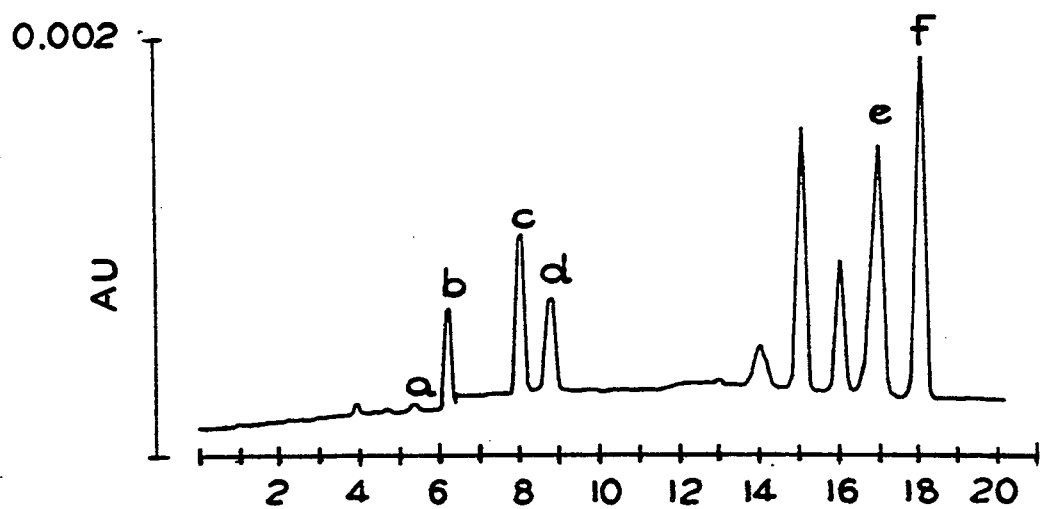
Figure 6C:

The separating power of HPE is further demonstrated in FIG. 6(A–C) in which combinations of two (A) and three (B) thiols have been separated from their S-nitrosated derivatives. These electropherograms were generated by mixing equimolar amounts of thiol mixture in 2-fold and 3-fold molar excess, respectively, over sodium nitrite.

In (A), equimolar (500 $\mu$M) homocysteine and cysteine were exposed to $NaNO_2$ in a 2:1 molar excess thiol over $NaNO_2$. The electropherogram demonstrates preferential S-nitrosation of homocysteine over cysteine (1.5:1). The four fully resolved peaks correspond to homocysteine (peak a) (176 $\mu$M), S-nitroso-homocysteine (peak b) (335 $\mu$M), cysteine (peak c) (295 $\mu$M) and S-nitroso-cysteine (peak d) (217 $\mu$M).

In (B), equimolar (1 mM) homocysteine, cysteine, and glutathione were exposed to $NaNO_2$ in a 3:1 molar excess thiol over $NaNO_2$. Homocysteine (peak b) (312 $\mu$M), cysteine (peak d) (528 $\mu$M), and glutathione (peak e) (206 $\mu$M) and S-nitroso-cysteine (not detected). The small peak corresponding to homocystine is also identified (peak a).

In (C), capillary electrophoretic detection of the sample in B at 320 nm demonstrates the presence of S-nitroso-homocysteine (peak a) and S-nitroso-glutathione (peak b). It is noteworthy that S-nitroso-glutathione and S-nitroso-homocysteine form at the expense of S-nitroso-cysteine.

DISCUSSION

These dam demonstrate that capillary electrophoresis provides a rapid and reproducible method for separating the biological thiols, their oxidized forms (specifically, disulfides and homocysteine thiolactone) and their S-nitrosated derivatives. This method of thiol detection and separation is superior to currently available methods because of its simplicity, general applicability, and the lack of a requirement for thiol derivatization. In the case of the biological S-nitrosothiols, this is a novel and reliable method for their separation and detection.

Commercially available preparations of glutathione elute as two fully resolved peaks (FIG. 1C), an observation that has been suggested by investigators to be consequence of significant contamination with glutathione disulfide. The following evidence supports the view that the early minor peak is glutathione disulfide and the major peak is reduced glutathione: (1) the predicted migration times of the disulfide and the reduced thiol on the basis of effective charge calculations are 13.2 and 16.9 min (Table I), respectively, closely corresponding to the observed elution times of the minor ($t_m = 14.2 \pm 0.4$ min, n=6) and major ($T_m = 16.3 \pm 0.4$ min, n=6) peaks; (2) carboxyamidation of glutathione's sulfhydryl group with iodoacemmide leads to the generation of a new peak with a migration time of $18.3 \pm 0.3$ min, closely approximating that predicted for a carboxyamidated glumthione conjugate ($t_p = 18.9$ min) (data not shown); (3) the strong reducing conditions engendered by preincubation of glutathione in a 14-fold molar excess of 2-mercaptoethanol (a neutral thiol that will not migrate electrophoretically) for 30 min eliminated the early peak (data not shown); and, most importantly, (4) the observed mobility of purified glutathione disulfide ($t_m = 13.4 \pm 0.3$ min, n=6) closely corresponds to that of the minor peak (FIG. 2C).

It has been demonstrated that certain S-nitrosothiols can form at a pH which is as high as 5, when experiments are conducted at 37° C. (Ignarro et al., J. Pharmacol. Exp. Ther. 218:739-749 (1981)). Therefore, in order to eliminate the possible artifactual formation of S-nitrosothiols under acidic pH, the inventors analyzed the pH and temperature dependence of the formation of S-nitrosothiols (specifically S-nitroso-L-cysteine from 50 mM $NaNO_2$ and 50 mM L-cysteine) at pH 5.0 and found that no more than 4.7% of L-cysteine is converted to S-nitroso-L-cysteine by 20 min when working at 4° C. Thus, in certain situations readily ascertainable by one of skill in the art, conducting capillary electrophoresis at lower temperatures and less acidic pH may be beneficial in preventing the artifactual formation of S-nitrosothiols, thereby further enhancing the accuracy of the analytic method. Furthermore, in the preparation of protein-containing biologic specimens, protein-precipitation with acetone or ether is preferable over trichloroacetic acid.

The simplicity and rapidity of electrophoresis renders it valuable for the detection of thiols and their S- nitrosated and oxidized derivatives. Furthermore, electrophoretic separation conducted under acidic conditions significantly improves specificity. In addition, detection methods such as thermooptical absorbance, electrochemical detection, and indirect fluorescence emission may be used in conjunction with electrophoretic techniques in order to further increase the detection capabilities of this analytic method (Yu et al., *Anal. Chem.* 61:37–40 (1989); Banks, P., *J. Natl. Inst. Health Res.* 2:87–89 (1990); Kahr et al., *Anal. Chem.* 60:1832–1834 (1988)).

TABLE I

MIGRATION TIMES AS PREDICTED FROM EFFECTIVE CHARGE (q/m) OF SELECTED BIOLOGICAL THIOLS AND THEIR S-NITROSATED DERIVATIVES[a]

|  | q | q/m | $t_p$ | $t_m$ (mean ± SD) |
|---|---|---|---|---|
| homocysteine | 0.44 | 0.0033 | std | 5.92 ± 0.15 |
| cysteine | 0.27 | 0.0022 | 8.80 | 8.34 ± 0.12 |
| glutathione | 0.35 | 0.0011 | 16.93 | 16.15 ± 0.30 |
| S-nitroso-homocysteine | 0.44 | 0.0027 | 7.20 | 7.74 ± 0.18 |
| S-nitroso-cysteine | 0.27 | 0.0018 | 11.03 | 12.14 ± 0.50 |
| S-nitroso-glutathione | 0.35 | 0.0010 | 18.55 | 18.20 ± 0.37 |

[a]q is the charge and was calculated at an assumed pH of 2.3; m is the mass for which molecular weight was substituted in calculations of effective charge; ;$t_p$ is the predicted migration time based on the homocysteine standard (std) in minutes (where $t_p = t_m$, homocysteine [q/m] homocysteine $[q/m]_p$), while $t_m$ is the corresponding measured migration time (mean ± SD, n = 3–8).

TABLE II

MIGRATION TIMES OF BIOLOGICAL THIOLS, OXIDIZED DERIVATIVES, AND S-NITROSOTHIOLS

|  | $t_m^a$ (mean ± SD) |
|---|---|
| homocysteine | 5.92 ± 0.15 |
| homocystine | 5.20 ± 0.10 |
| homocysteine thiolactone (free base) | 2.53 ± 0.08 |
| homocysteine thiolactone (hydrochloride) | 1.65 ± 0.06 |
| cysteine | 8.34 ± 0.12 |
| cystine | 8.30 ± 0.04 |
| glutathione | 16.15 ± 0.30 |
| glutathione disulfide | 13.40 ± 0.34 |
| N-acetylcysteine[b] | 2.42 ± 0.06 |
| S-nitroso-homocysteine | 7.74 ± 0.18 |
| S-nitroso-cysteine | 12.14 ± 0.5 |
| S-nitroso-glutathione | 18.20 ± 0.37 |
| S-nitroso-N-acetylcysteine[b] | 2.50 ± 0.06 |

[a]Migration times ($t_m$ mean ± SD) in minutes are based on n = 5–8. Under these conditions a bradykinin standard eluted at $t_m$ = 2.70 ± 0.03 min. Electrophoretic mobility (cm$^2$/(s/V)) can be related to $t_m$ by the relationship $\mu_e = L^2/tV = 5.39 \times 10^{-4}/t_m$ substituting $L_dL_t$ for $L^2$ where $L_d$ is the length of the capillary from sample injection site to detector and $L_t$ is the full capillary length.
[b]Conditions for N-acetylcysteine and S-nitroso-N-acetylcysteine were exceptional (see text for details).

TABLE III

LINEARITY OF PEAK HEIGHT VS CONCENTRATION OF THIOLS, OXIDIZED DERIVATIVES, AND S-NITROSOTHIOLS

|  | linear eq | corr coeff (R) |
|---|---|---|
| homocysteine | Y = 2.98X − 0.0000016 | 1.000 |
| homocystine | Y = 1.74X + 0.000014 | 0.999 |
| homocysteine thiolactone | Y = 11.6X − 0.000014 | 0.999 |
| cysteine | Y = 47.3X + 0.000332 | 0.998 |
| cystine | Y = 4.90X + 0.0000036 | 0.990 |
| glutathione | Y = 3.60X + 0.000025 | 0.999 |
| glutathione disulfide | Y = 10.3X + 0.0000065 | 0.995 |
| N-acetylcysteine | Y = 6.36X + 0.0000062 | 0.996 |
| S-nitroso-homocysteine | Y = 3.07X − 0.0000059 | 0.999 |
| S-nitroso-cysteine | Y = 6.44X + 0.000041 | 0.990 |
| S-nitroso-glutathione | Y = 9.992X − 0.000039 | 0.993 |
| S-nitroso-N-acetylcysteine | Y = 5.99X + 0.000010 | 0.995 |

TABLE III-continued

LINEARITY OF PEAK HEIGHT VS CONCENTRATION OF THIOLS, OXIDIZED DERIVATIVES, AND S-NITROSOTHIOLS

|  | linear eq | corr coeff (R) |
|---|---|---|

[a]The X value of each equation refers to the concentration of each molecular species (in mol/L) and the Y value refers to the peak amplitude in absorbance units (at 200 nm). The slope of each equation is expressed in absorbance units-L/mole, and Y intercept in absorbance units.

What is claimed is:

1. A method for separating and detecting individual thiol compounds in a biological sample comprising subjecting said sample to capillary electrophoresis.

2. A method for separating and detecting individual thiol compounds in a biological sample comprising the steps:
    (a) determining the elution time of known individual thiols to establish thiol standards:
    (b) subjecting said biological sample to capillary electrophoresis; and
    (c) comparing the elution times obtained for each component present in the sample, to the known elution times of the thiol standards prepared in step (a), to determine the identity of each individual thiol compound present in the sample.

3. A method tbr separating and detecting individual S-nitrosothiol compounds in a biological sample comprising subjecting said sample to capillary electrophoresis.

4. A method for separating and detecting individual S-nitrosothiol compounds in a biological sample comprising the steps:
    (a) determining the elution time of known individual S-nitrosothiols to establish S-nitrosothiol standards;
    (b) subjecting said biological sample to capillary electrophoresis; and
    (c) comparing the elution times obtained for each component present in the sample to the known elution times of the S-nitrosothiol standards prepared in step (a), to determine the identity of each individual thiol compound present in the sample.

5. A method for separating and detecting oxidized derivatives of individual S-nitrosothiol compounds in a biological ample comprising subjecting said sample to capillary electrophoresis.

6. A method for separating and detecting oxidized derivatives of individual S-nitrosothiol compounds in a biological sample comprising the steps:
    (a) determining the elution time of known oxidized derivatives of individual thiol compounds to establish oxidized derivative standards;
    (b) subjecting said biological sample to capillary electrophoresis; and
    (c) comparing the elution times obtained for each compound present in the sample to the known elution times of the oxidized derivative standards prepared in step (a), to determine the identity of each individual oxidized thiol derivative present in the sample.

7. The method of any one of claims 1–6 wherein the sample is treated with an acid just prior to subjecting it to capillary electrophoresis.

8. The method of claim 7 wherein treatment of said sample with acid results in a sample pH between 2.0 and 6.8.

9. The method of any one of claims 1–6 wherein said biological sample is selected from the group consisting of blood, serum, urine, cerebrospinal fluid, semen, synovial fluid, peritoneal fluid, sputum, intestinal secretions, corneal fluid, amniotic fluid, stool, saliva and sweat.

10. The method of any one of claims 1–6 wherein said capillary electrophoresis is conducted at a temperature of 4° C.–37° C.

11. A method for monitoring the extent of a disease state associated with abnormal levels of nitric oxide, nitrosonium or nitroxyl, comprising the method of claim 3 to monitor S-nitrosothiol levels in the biological fluids of a patient.

12. The method of claim 11 wherein said disease state is selected from the group comprised of septic shock, cardiogenic shock, hypovolemic shock, atherosclerosis, hyperhomocysteinemia, venous thrombosis, arterial thrombosis, coronary occlusion, pulmonary embolism, cerebrovascular accidents, vascular fibrosis, ectopia lentis, osteoporosis, mental retardation, skeletal deformities, pulmonary hypertension, malignancy, infections and central nervous system disorders, renal disorders, respiratory disorders and gastrointestinal diseases.

* * * * *